United States Patent [19]

Mimura et al.

[11] 4,450,233

[45] May 22, 1984

[54] IMMOBILIZATION OF MICROORGANISMS IN A POLYMER GEL

[75] Inventors: Akio Mimura; Katsumi Yuasa; Mitsuru Shibukawa, all of Shizuoka, Japan

[73] Assignee: Asahi Kasei Kogyo Kabushiki Kaisha, Osaka, Japan

[21] Appl. No.: 330,916

[22] Filed: Dec. 15, 1981

[30] Foreign Application Priority Data

Dec. 23, 1980 [JP] Japan .................................. 55-181383

[51] Int. Cl.³ ...................... C12N 11/10; C12N 11/08; C12N 11/04
[52] U.S. Cl. .................................... 435/178; 435/180; 435/182
[58] Field of Search ............... 435/174, 178, 179, 180, 435/182

[56] References Cited

U.S. PATENT DOCUMENTS 4,115,332  9/1978  Young et al. ..................... 260/17.4
4,338,401  7/1982  Cremonesi ......................... 435/178

OTHER PUBLICATIONS

Jack et al., The Immobilization of Whole Cells, Advances in Biochem. Eng. vol. 5, 1977 (pp. 126–135).

*Primary Examiner*—David M. Naff
*Attorney, Agent, or Firm*—Sughrue, Mion, Zinn, MacPeak & Seas

[57] ABSTRACT

Microorganisms are immobilized by adding microorganism cells to an aqueous solution of a mixture of a polymerizable starch and a polymerizable monomer, and, thereafter, polymerizing the polymerizable starch and polymerizable monomer, to prepare a polymer gel with microorganism cells enclosed therein. The polymerizable starch is prepared by introducing an acrylamidomethyl group into starch. The polymer gel has high mechanical strength and can be used repeatedly over long periods of the time while maintaining at high levels the reactivity of the microorganism enclosed therein.

6 Claims, No Drawings

IMMOBILIZATION OF MICROORGANISMS IN A POLYMER GEL

FIELD OF THE INVENTION

The present invention relates to a process for the production of immobilized microorganisms. More particularly, it is concerned with a process for the production of immobilized microorganisms which comprises adding microorganism cells to an aqueous solution of a mixture of a polymerizable starch and a polymerizable monomer and, thereafter, polymerizing the mixture to prepare a polymer gel with the microorganism cell enclosed therein.

BACKGROUND OF THE INVENTION

Immobilized microorganisms exhibit the activity of the enzymes contained in the microorganism cells, and can often be used repeatedly over long periods of time. In some uses, these immobilized microorganisms are commercially advantageous over immobilized enzymes prepared by binding purified enzymes onto a resinous carrier.

Various methods have long been known for the production of immobilized microorganisms. In accordance with a typical method, the immobilization is performed by enclosing microorganism cells with gels, such as polyacrylamide gel, agar gel, carrageenan gel, collagen gel, calcium alginate gel, and polyvinyl alcohol gel (see I. Senhata, Ed., *Immobilized Enzymes*, Kodansha, Tokyo (1975)).

Immobilization of microorganism cells per se permits the omission of the step of extracting and purifying enzymes contained in the microorganism cells, because the enzyme can be used as it is as an enzymatic agent, and the yield of enzyme activity can be maintained at high levels.

Enclosing microorganism cells per se in polymeric gel, however, gives rise to the problems that the enzyme reactivity is reduced, and, when the degree of enclosing of the polymeric gel is lowered to increase the enzyme reactivity, the physical strength of the gel per se is deteriorated. It has therefore been desired to discover gels which can be commercially used over long periods of time.

SUMMARY OF THE INVENTION

The principal object of the invention is to provide a process for the production of gels having high mechanical strength which can be used repeatedly over long periods of time while maintaining the reactivity of enzyme enclosed therein at high levels.

It has now been found that such gels can be prepared from a polymerizable starch which is prepared by introducing an acrylamidomethyl group into starch.

The present invention, therefore, provides a process for the production of immobilized microorganisms which comprises adding microorganism cells to an aqueous solution of a mixture of a polymerizable starch and a polymerizable monomer, said polymerizable starch being prepared by introducing an acrylamidomethyl group in starch, and, thereafter, polymerizing the mixture, to thus prepare a polymer gel with microorganism cells enclosed therein.

DETAILED DESCRIPTION OF THE INVENTION

The polymerizable starches as used herein include known commercially available polymerizable starches. For example, one is sold under the trade mark of Starpol-100. This product is manufactured by A. E. Staley Manufacturing Co., U.S.A., and is used as an additive for a coating agent or adhesive.

Copolymerization of the polymerizable starch with polymerizable monomers such as vinyl monomers (e.g., acrylamide, acrylic acid, hydroxymethylacrylic acid, and N,N'-methylenebisacrylamide) can be performed at relatively low temperatures in the presence of polymerization accelerators, such as amines (e.g., $\beta$-dimethylaminopropionitrile). The copolymerization can be initiated by methods conventionally employed in the polymerization of acrylamide, for example, by irradiation with ultraviolet rays, radiation rays (e.g. X ray, $\gamma$ ray, etc.), and the like, or by the addition of peroxides such as potassium persulfate.

As is described above, gels having high mechanical strength and being capable of maintaining the reactivity of enzyme enclosed therein at high levels can be produced using the polymerizable starch. The amount of the polymerizable starch to be copolymerized is generally from 5 to 80 wt%, preferably from 10 to 80 wt%, based on the total weight of the polymerizable starch and the polymerizable monomer.

The microorganism cell to be immobilized according to the invention can be appropriately selected from cells of bacteria, fungi, actinomyces, yeast fungi, etc. These microorganism cells may be cells of living microorganisms which are cultivated on a culture medium by a conventional method, or powdery cells of dried microorganisms which are prepared by a freeze-drying treatment or a treatment using an organic solvent such as acetone. The microorganism cell can be appropriately selected depending on the purpose for which the ultimate immobilized microorganism is to be used.

Hereinafter the invention will be described in more detail by reference the steps of the process of the invention.

Microorganism cells to be immobilized are prepared by cultivating the microorganism under cultivation conditions which are most suitable for production of the desired enzyme system, separating the microorganism cells from the fermentation broth by a method such as a centrifugal separation method, and, if necessary, by washing the microorganism cells with water, a buffer, or the like.

The living or dried microorganism cells are added in an aqueous solution of a mixture of a polymerizable starch and a polymerizable monomer so that they are enclosed in the formed gel in an amount of 20 g or less per 100 g (wet) of the formed gel.

Gelation can be effected by the known gel enclosing method. For example, a vinyl monomer, such as acrylamide or N,N'-methylenebisacrylamide, is dissolved in an aqueous solution of polymerizable starch, for example, Starpol-100, and a predetermined amount of the microorganism cell is added thereto. Then, the polymerizable starch and the vinyl monomer are polymerized at a low temperatures, e.g., 35° C. or less, in the presence of a polymerization accelerator (e.g., $\beta$-dimethylaminopriopionitrile) and a polymerization initiator (e.g., potassium persulfate).

The thus-formed gel is shaped into granules having an averge diameter of from 2 to 5 mm by, for instance, passing the gel through a wire net having openings of 2 to 5 mm twice. The thus shaped gel is then appropriately washed with water or a buffer whereby the desired immobilized microorganism gel can be prepared.

Although the thus prepared immobilized microorganism gel can be charged in to a reactor and used without the application of additional treatments, the activity of the enzyme system in the immobilized microorganism gel can be increased prior to the use thereof by suspending it in a microorganism fermentation broth or surface active agent-containing solution. Additionally, the fermentation production using the immobilized microorganism gel can be performed by inoculating a microorganism culture medium with the immobilized microorganism gel in the same manner as in a conventional fermentation procedure, and by applying procedures such as aerobic stirring. When the concentration of microorganism in the gel is low, it is possible to increase the concentration by suspending and cultivating the gel in a microorganism culture medium which is suitable for the growth of the enzyme system.

The immobilized microorganism prepared by the process of the invention can be used in various microorganism enzyme catalyzed reactions, for example, for the production of malic acid by the use of Brevibacterium ammoniagenes having furamase activity, the production of L-tryptophan by the use of Escherichia coli, etc., having triptophanase activity, and the production of semi-synthetic cephalosporin by the use of Bacillus megaterium having penicillin acylase activity. Additionally, antibiotics such as bacitracin can be produced by the use of Bacillus licheniformis, and amino acids such as L-glutamic acid can be produced by the use of Microbacterium ammoniaphilum.

The mechanical strength of the immobilized microorganism gel prepared by the process of the invention is high compared with those of the conventional polyacrylamide gel, potassium alginate gel, agar gel, and collagen gel, and furthermore, the activity of the microorganism cells immobilized in the gel can be maintained at high levels. Thus, the process of the invention permits commercial utilization of immobilized microorganisms.

The following examples are given to illustrate the invention in greater detail, although the invention is not limited thereto. Percentages and ratios are by weight unless otherwise indicated.

EXAMPLE 1

Five milliliters of a sterilized culture medium (pH: 7.0) containing 2% glucose, 0.2% urea, 0.2% potassium monophosphate, 0.05% magnesium sulfate, 1% corn steep liquor, and 5% fumaric acid was inoculated with Brevibacterium ammoniagenes ATCC 6871("ATCC" refers to the American Type Culture Collection Number), and was then incubated at 30° C. for 24 hours. On the other hand, ten 100 ml-culture mediums having the same composition as described above were placed in a 500 ml shaking flask and sterilized, respectively. Each 100 ml of the culture medium was then inoculated with 5 ml of the seed culture as prepared above, and incubated at 30° C. for 24 hours while shaking. After the cultivation was completed, the fermentation broths were combined to make 1 liter, and the combined fermentation broth was subjected to centrifugal separation to collect cells.

Five grams of polymerizable starch (Starpol-100) was suspended in 50 ml of water and dissolved therein by heating at 95° C. to prepare a transparent aqueous solution of the polymerizable starch. After the aqueous solution was cooled to room temperature, 15 g of acrylamide was added thereto and throughly dissolved therein. Thereafter, the above prepared living cells of Brevibacterium ammoniagenes were added to the aqueous solution of the polymerizable starch and acrylamide, and thoroughly mixed therewith.

Water was added to the resulting solution to make the total volume 85 ml, and then, 10 ml of a 5% aqueous $\beta$-dimethylaminopropionitrile solution as a polymerization accelerator and 5 ml of a 2.5% aqueous potassium persulfate solution as a polymerization initiator were added and throughly mixed therewith. Polymerization was performed by allowing the mixture to stand at 15° C. for 15 hours.

The thus prepared elastic gel with the microorganism cells enclosed therein was formed into small gel particles having a diameter of about 2 mm by passing it through a wire net with 2 mm×2 mm meshes, and washed with 2 liters of water to obtain 107 g of immobilized microorganism gel material.

To 200 ml of a 1/15 mole phosphate buffer solution (pH: 7.5) were added 32 g of sodium fumarate, 0.02 g of cetyl pyridinium chloride, and 107 g of the above prepared immobilized microorganism gel, which were then reacted at 35° C. for 24 hours while shaking. After the reaction was completed, the immobilized microorganism gel material was filtered off and washed with 1 liter of water.

L-malic acid contained in the reaction solution from which the immobilized microorganism gels had been removed, and the water which had been used for washing the immobilized microorganism gels was measured by a microbiological determination method using Lactobacillus arabinosus. This analysis showed that 19.0 g of L-malic acid was formed. The yield was 72 mole% based on the fumaric acid added.

EXAMPLE 2

Living cells of Brevibacterium ammoniagenes ATCC 6871 were prepared using 5 liters of a culture medium in the same manner as in Example 1, and divided into five 1-liter portions.

These living cells were immobilized in the same manner as in Example 1, except that the amounts of the polymerizable starch (Starpol-100) and acrylamide added were changed as shown in Table 1 to thereby prepare the corresponding immobilized microorganism cells. The relative amounts of the microorganism cells, polymerization accelerator, and polymerization initiator added were the same as in Example 1. The wet weight of each of the immobilized microorganism gels is shown in Table 1. Using each immobilized microorganism gel, the reaction was performed in the same manner as in Example 1. The results are shown in Table 1.

TABLE 1

| Starpol-100 (g) | Acrylamide (g) | Amount of Immobilized Microorganism Gel (g) | Amount of L-Malic Acid formed (g) |
| --- | --- | --- | --- |
| 20 | 0 | 95 | 16.3 |
| 15 | 5 | 107 | 18.8 |
| 10 | 10 | 105 | 18.7 |
| 5 | 15 | 105 | 19.5 |

TABLE 1-continued

| Starpol-100 (g) | Acrylamide (g) | Amount of Immobilized Microorganism Gel (g) | Amount of L-Malic Acid formed (g) |
|---|---|---|---|
| 3 | 17 | 100 | 18.2 |

As shown in Table 1, a large amount of L-malic acid was formed using the gel prepared from 15 to 75% of the polymerizable starch based on the total weight of the polymerizable starch and acrylamide.

EXAMPLE 3

Living cells of Brevibacterium ammoniagenes ATCC 6871 were prepared using 4 liters of a culture medium in the same manner as in Example 1, and divided into four 1-liter portions.

Twenty grams of polymerizable starch (Starpol-100) was suspended in 200 ml of water and dissolved therein by heating at 95° C. to prepare a transparent aqueous solution of the polymerizable starch. After being cooled to room temperature, the aqueous solution of the polymerizable starch was divided into four portions. To these aqueous solutions were added acrylamide, sodium acrylate, sodium hydroxymethylacrylate, and N,N'-methylenebisacrylamide, respectively, in amounts of 5 g each, and dissolved therein.

The 4 portions of living cells of Brevibacterium ammoniagenes were added respectively, to the 4 aqueous solutions noted above and fully mixed therewith. After adding water thereto to make the total volume 85 ml, 10 ml of a 5% aqueous β-dimethylaminopropionitrile as a polymerization accelerator and 5 ml of 2.5% potassium persulfate as a polymerization initiator were added and well mixed therewith. Polymerization was performed by allowing the mixture to stand at 20° C. for 15 hours.

The thus prepared elastic gel with the microorganism cells enclosed therein was formed into small gel particles having an average diameter of about 2 mm by passing it through a wire net with 2 mm×2 mm meshes, and washed with 2 liters of water. The wet weight of the gel is shown in Table 2.

An aqueous solution was prepared by dissolving 128 g of sodium fumarate and 0.08 g of cetyl pyridinium chloride in 800 ml of a phosphate buffer solution (1/15 moles: pH: 7.5), and divided into four portions. The above prepared immobilized microorganism gel was suspended in each of the aqueous solutions, and the reaction was conducted at 37° C. for 24 hours while shaking. After the reaction was completed, the immobilized microorganism gel was filtered off and washed with 1 liter of water. L-malic acid contained in the reaction solution from which the immobilized microorganism gel had been removed, and the water which had been used to wash the immobilized microorganism gel was measured, and the results are shown in Table 2.

TABLE 2

| Vinyl Monomer | Amount of Immobilized Microorganism Gel (g) | Amount of L-Malic Acid formed (g) |
|---|---|---|
| Acrylamide | 105 | 19.3 |
| Sodium Acrylate | 97 | 18.1 |
| Sodium Hydroxymethylacrylate | 110 | 18.8 |
| N,N'—Methylenebisacrylamide | 113 | 18.4 |

As shown in Table 2, acrylamide, sodium acrylate, sodium hydroxymethylacrylate, and N,N'-methylenebisacrylamide were effective as the vinyl monomer to be copolymerized with the polymerizable starch.

EXAMPLE 4

In a reaction solution composed of 200 ml of a phosphate buffer solution (1/15 moles; pH: 7.5), 32 g of sodium fumarate, and 0.02 g of cetyl pyridinium chloride was suspended 105 g of an immobilized microorganism gel which had been prepared in the same manner as in Example 1. The suspension was placed in a 1.2-liter minijar fermenter (Model MD-150, produced by Marubishi Rika Co.) and the reaction was performed at 35° C. for 24 hours while stirring.

After 24 hours from the start of the reaction, a phosphate buffer solution (1/15 mole; pH: 7.5) containing 16% of sodium fumarate and 0.01% of cetyl pyridinium chloride was continuously introduced while at the same time withdrawing an equal amount of reaction solution, thus initiating a continuous reaction. In this continuous reaction, the average residence time was adjusted to 24 hours.

The reaction solution withdrawn from the reactor was collected every 24 hours, and the content of L-malic acid formed was analyzed. As shown in Table 3, even after the continuous reaction was effected for 20 days, there was no significant change in the amount of L-malic acid formed.

TABLE 3

| Days for which Continuous Reaction was performed | Amount of L-Malic Acid formed (per 24 hours) (g) |
|---|---|
| 1 | 14.1 |
| 3 | 19.6 |
| 7 | 19.0 |
| 10 | 18.2 |
| 13 | 18.5 |
| 17 | 18.3 |
| 20 | 17.4 |

EXAMPLE 5

Five milliliters of a culture medium (pH: 7.2) containing 2% peptone, 1% casamino acid, 0.5% yeast extract, 5% corn steep liquor, 0.2% L-tryptophne, 0.05% potassium monophosphate, 0.05% magnesium sulfate, 0.003% ferrous sulfate, and 0.003% manganese sulfate was placed in a test tube having a diameter of 18 mm, sterilized at 120° C. for 10 minutes, inoculated with a platinum-loop full of Enterobacter species AST 49-4 (ATCC 31901; FERM-P No. 5543) ("FERM" referred to Fermentation Research Institute, Agency of Industrial Science and Technology, Japan), and incubated at 32° C. for 20 hours while shaking, to thereby prepare a seed culture. On the other hand, twenty 100 ml-culture mediums having the same composition as described above were placed in a 500-ml shaking flask and sterilized at 120° C. for 10 minutes, respectively. Each 100 ml of the culture medium was then inoculated with 5 ml of the seed culture as prepared above, and incubated at 32° C. for 20 hours. After the cultivation was completed, 2 liters of the fermentation broth was subjected to centrifugal separation to collect the living cells.

7.5 g of polymerizable starch (Starpol-100) was suspended in 50 ml of water, and dissolved therein by heating at 98° C., to prepare a transparent aqueous solution of the polymerizable starch. After the aqueous solution was cooled to room temperature, 12.5 g of acrylamide was added to the aqueous solution and dissolved therein. The above prepared living cells of Enterobacter species AST 49-4 were added to the solution and well mixed therewith. Water was added to the solution to make the total volume 85 ml. Thereafter, 10 ml of a 5% aqueous β-dimethylaminopropionitrile solution as a polymerization accelerator and 5 ml of a 2.5% aqueous potassium persulfate solution as a polymerization initiator were added and well mixed thereto. Polymerization was performed by allowing the resulting mixture to stand at 15° C. for 15 hours. The thus prepared elastic gel was formed into small gel particles having an average diameter of about 2 mm by passing it through a wire net having 2 mm×2 mm meshes, and washed with 2 liters of water to obtain 112 g of an immobilized microorganism gel.

In 200 ml of a reaction solution (pH: 9.0) having the composition comprising 20 g of sodium pyruvate, 20 g of ammonium acetate, 20 g of indole, 100 mg of pyridoxal phosphate, 2 g of ethylenediamine tetraacetate, 900 ml of water, and 100 ml of methanol was suspended 112 g of the above prepared immobilized microorganism gel with Enterobacter species AST 49-4 enclosed therein, and the reaction was performed at 32° C. while shaking. After 36 hours, the immobilized microorganism gel was separated from the reaction solution by filtration, and it was again suspended in 200 ml of the same reaction solution as above to repeat the reaction. In the same manner, the reaction was repeated seven times. There was no change in the amount of L-tryptophane formed, as is shown in Table 4.

TABLE 4

| Number of Reaction | Yield of L-Tryptophane (per 36 hour reaction) (g) |
|---|---|
| 1st | 4.4 |
| 2nd | 5.4 |
| 3rd | 6.0 |
| 4th | 5.6 |
| 5th | 5.3 |
| 6th | 5.1 |
| 7th | 5.2 |

EXAMPLE 6

Fifty milliliters of a culture medium (pH: 7.8) containing 2% soluble starch, 0.5% glucose, 1% peptone, 5% hydrochloric acid hydrolyzate of de-fatted soybeans, and 0.5% magnesium sulfate was sterilized, inoculated with Baccilus licheniformis ATCC 10716, and incubated at 32° C. for 16 hours to prepare a seed culture. On the other hand, two 100 ml-culture mediums having the same composition as above were placed in a 500-ml shaking flask and sterilized, respectively. Each 100 ml of the culture medium was then inoculated with 5 ml of the above prepared seed culture, and incubated at 32° C. for 13 hours while shaking. After the cultivation was completed, 200 ml of the fermentation broth was subjected to centrifugal separation to collect the living cells.

In 80 ml of water was suspended 5 g of polymerizable starch (Starpol-100) and dissolved therein by heating at 100° C. for 10 minutes to prepare an aqueous solution of the polymerizable starch. After the aqueous solution was cooled to 20° C., 15 g of acrylamide was added thereto, and thoroughly dissolved therein. The above prepared living cells of Bacillus licheniformis which produces polypeptide antibiotic bacitracin were added to the mixture, and 10 ml of a 5% aqueous β-dimethylaminopropionitrile solution as a polymerization accelerator and 5 ml of a 2.5% aqueous potassium persulfate solution as a polymerization initiator were added and thoroughly mixed therewith. Polymerization was performed by allowing the mixture to stand at 20° C. for 10 hours.

The thus-prepared elastic gel was formed into small gel particles having a diameter of about 2 mm by passing it through a wire net having 2 mm×2 mm meshes and was well washed with 2 liters of water which had been sterilized by heating. Then, 50 g of the gel was suspended in 100 ml of a culture medium having the same composition as above, and shaking cultivation was performed at 32° C. for 23 hours. After the cultivation was completed, the gel was separated from the fermentation broth by an aseptic procedure, and again suspended in a freshly prepared culture medium having the same composition as described above. In the same manner, the shaking cultivation was repeated eight times. Bacitracin produced in the culture medium was identified by a thin layer chromatography using silica gel and estimated by a conventional method of growth inhibition test using Micrococcus flavus ATCC 10240. The results are shown in Table 5.

TABLE 5

| Number of Cultivation | Amount of Bacitracin formed (units/ml) |
|---|---|
| 1st | 153 |
| 2nd | 189 |
| 3rd | 191 |
| 4th | 173 |
| 5th | 182 |
| 6th | 177 |
| 7th | 168 |
| 8th | 170 |

While the invention has been described in detail and with reference to specific embodiments thereof, it will be apparent to one skilled in the art that various changes and modifications can be made therein without departing from the spirit and scope thereof.

What is claimed is:

1. A process for producing an immobilized microorganism, comprising adding microorganism cells to an aqueous solution of a mixture of a polymerizable starch and a polymerizable vinyl monomer, said polymerizable starch being prepared by introducing an acrylamidomethyl group into starch and said polymerizable starch being present in an amount of about 5 to 80 weight percent based on the total weight of the polymerizable starch and the polymerizable monomer, and thereafter, polymerizing the mixture, to prepare a polymer gel with microorganism cells enclosed therein.

2. A process as in claim 1, wherein the polymerizable monomer is at least one vinyl monomer selected from the group consisting of acrylamide, acrylic acid, hydroxymethylacrylic acid, and N,N'-methylenebisacrylamide.

3. A polymer gel containing immobilized microorganisms made by a process comprising adding microorganism cells to an aqueous solution of a mixture of a polymerizable starch and a polymerizable vinyl monomer, said polymerizable starch being prepared by introducing an acrylamidomethyl group into starch and said polymerizable starch being present in an amount of about 5 to 80 weight percent based on the total weight of the polymerizable starch and the polymerizable monomer, and, thereafter, polymerizing the mixture to prepare a polymer gel with microorganism cells enclosed therein.

4. A polymer gel as in claim 3, wherein the polymerizable monomer is at least one vinyl monomer selected from the group consisting of acrylamide, acrylic acid, hydroxymethylacrylic acid, and N,N'-methylenebisacrylamide.

5. The process of claim 1 wherein said polymerizing is initiated by a peroxide.

6. The polymer gel of claim 3 wherein said polymerizing is initiated by a peroxide.

* * * * *